(12) United States Patent
Stamler et al.

(10) Patent No.: US 6,964,984 B2
(45) Date of Patent: *Nov. 15, 2005

(54) PREVENTING DESENSITIZATION OF RECEPTORS

(75) Inventors: Jonathan S. Stamler, Chapel Hill, NC (US); Robert J. Lefkowitz, Durham, NC (US); Erin J. Whalen, Durham, NC (US); Walter J. Koch, Durham, NC (US); Claude A. Piantadosi, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/608,120

(22) Filed: Jun. 30, 2003

(65) Prior Publication Data

US 2004/0053852 A1 Mar. 18, 2004

Related U.S. Application Data

(63) Continuation of application No. 10/280,085, filed on Oct. 25, 2002, now Pat. No. 6,627,602, which is a continuation-in-part of application No. 09/986,807, filed on Nov. 13, 2001, now Pat. No. 6,472,390.

(51) Int. Cl.[7] .............................................. A61K 31/13
(52) U.S. Cl. ....................................... 514/645; 514/670
(58) Field of Search ............................ 514/2, 645, 670

(56) References Cited

U.S. PATENT DOCUMENTS

| | | | |
|---|---|---|---|
| 5,385,937 A | 1/1995 | Stamler et al. | |
| 5,574,068 A | 11/1996 | Stamler et al. | 514/562 |
| 5,873,359 A | 2/1999 | Zapol et al. | |
| 5,968,911 A | 10/1999 | Lawson et al. | 514/54 |
| 5,985,862 A | 11/1999 | Tjoeng et al. | 514/171 |
| 6,057,367 A | 5/2000 | Stamler et al. | |
| 6,063,407 A | 5/2000 | Zapol et al. | |
| 6,139,847 A | 10/2000 | Chobanian et al. | 424/400 |
| 6,297,260 B1 | 10/2001 | Bandarage et al. | 514/327 |
| 6,314,956 B1 | 11/2001 | Stamler et al. | |
| 6,337,321 B1 | 1/2002 | Cooke et al. | |
| 6,340,480 B1 | 1/2002 | Duckett et al. | |
| 6,358,536 B1 | 3/2002 | Thomas | |
| 6,472,390 B1 | 10/2002 | Stamler et al. | 514/236.5 |
| 6,482,846 B1 | 11/2002 | Garvey et al. | 514/413 |
| 6,486,206 B1 | 11/2002 | Lurie | 514/561 |
| 6,617,355 B1 | 9/2003 | Gaston et al. | |
| 6,627,602 B2 * | 9/2003 | Stamler et al. | 514/2 |
| 2001/0012834 A1 | 8/2001 | Stamler | 514/18 |
| 2002/0010146 A1 | 1/2002 | Garvey et al. | 514/44 |
| 2002/0128205 A1 | 9/2002 | Stamler et al. | |
| 2003/0212004 A1 | 11/2003 | Gaston et al. | |

FOREIGN PATENT DOCUMENTS

WO  WO 02/32418  4/2002

OTHER PUBLICATIONS

Nozik–Grayck et al. (2002). *Am. J. Physiol. Lung Cell Mol. Physiol.* 282: L1057–L1065.
Copy of International Search Report for PCT/US02/25937 (Jan. 2003).
Copy of Published International Search Report for PCT/US03/029134 (Jun., 2004).

* cited by examiner

Primary Examiner—Raymond J. Henley, III
(74) Attorney, Agent, or Firm—Mintz Levin Cohn Ferris Glovsky and Popeo, P.C.; Ivor R. Elrifi

(57) ABSTRACT

Desensitization of receptors that control disease is prevented by inhibiting G-protein receptor kinases. This has applicability, e.g., for patients with heart failure or on a left ventricular heart device or a heart pump after surgery or about to undergo surgery and at high risk for a cardiac event or on an opiate or addicted to opiate or with cystic fibrosis or rheumatoid arthritis.

2 Claims, 3 Drawing Sheets

Figure 1:
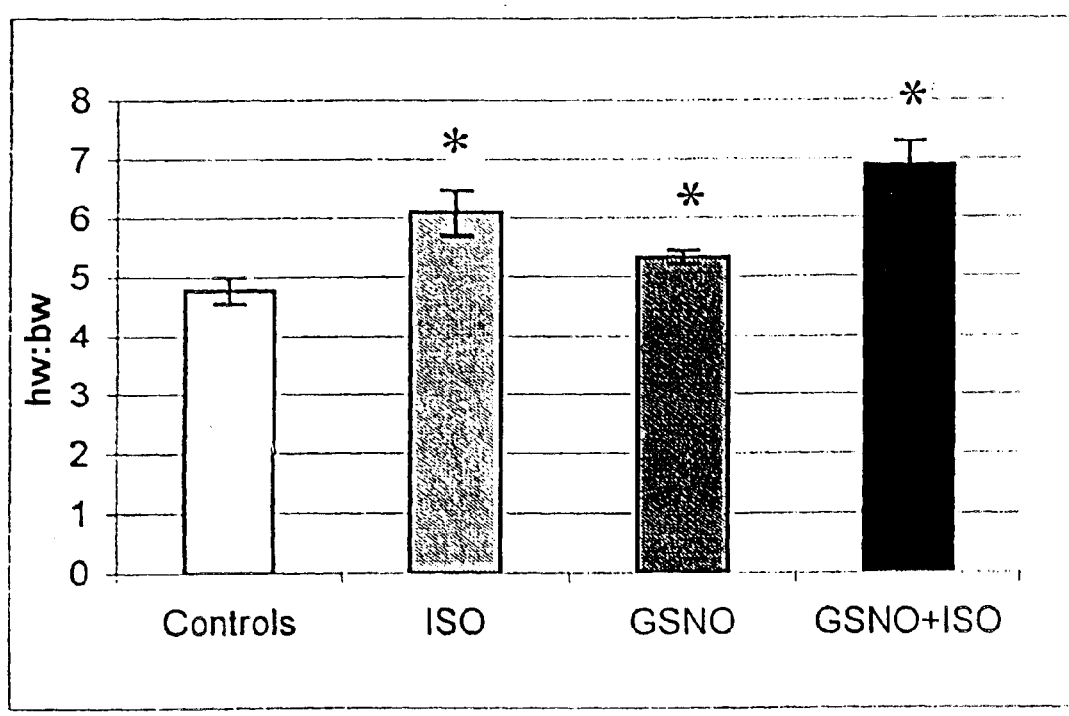

PREVENTING DESENSITIZATION OF RECEPTORS

CROSS-REFERENCE TO RELATED APPLICATION

This is a continuation of U.S. application Ser. No. 10/280,085, filed on Oct. 25, 2002 now U.S. Pat. No. 6,627,602, which in turn is a continuation-in-part of U.S. application Ser. No. 09/986,807, filed on Nov. 13, 2001, now U.S. Pat. No. 6,472,390.

TECHNICAL FIELD

The invention herein is directed to prevention of desensitization of receptors to activation by agonists.

BACKGROUND OF THE INVENTION

Many receptors which are involved in controlling pathologic conditions are coupled to G-proteins (Pierce, K. L., et al, Nature Review (Molecular Cell Biology) 3, 639–650 (2002)). These are called G-protein coupled receptors (GPCRs). The GPCRs include α-adrenergic receptors, β-adrenergic receptors, opioid receptors and prostaglandin receptors. Over time, when agonists are administered to activate the receptors, the receptors become desensitized, i.e., agonist administration no longer results in therapeutic activation of receptors and the receptors regardless of agonist administration are unable to control the pathologic condition.

SUMMARY OF THE INVENTION

It is known that when agonist binds to a GPCR to activate it, the sequence of events is that the receptor is phosphorylated, the phosphorylated receptor moves to the interior of the cell it is associated with, i.e., it is internalized, with the internalization often involving recruitment of β-arrestin and then the receptor is recyled and moves to the surface of the cell housing it where it is available to control a disease event and to bind to agonist for activation for control of the disease event. The GPCRs have G-protein receptor kinases (GRKs) associated with them. The GRKs phosphorylate agonist-occupied receptors thereby promoting binding of β-arrestin molecules which inhibit interactions between the receptors and G-proteins while also promoting internalization of the receptors. GRKs thus dampen signaling by the GPCRs. The typical response is decreased level of GPCRs and desensitization thereof, (i.e., inability of agonist to activate the receptor and inability of the GPCRs to control the disease event). It has been discovered herein that nitric oxide donors (NO donors) that donate nitric oxide or a related redox species and provide bioactivity that is identified with nitric oxide, preferably S-nitrosoglutathione (GSNO), inhibit the GRKs dramatically thereby allowing GPCRs to signal and to be recycled to the cell surface, i.e., thus preventing desensitization of the GPCRs and allowing GPCRs to be available in sufficient amount to control the disease event. It has also been discovered herein that administration of GSNO results in growth of heart muscle (hypertrophy) in vivo (which can be both dependent and independent of expression of receptors) and prevents cardiac β-adrenergic receptor down regulation after chronic administration of a βadrenergic agonist.

The above discoveries support the invention herein which is directed to a method for treating a patient with a disease or pathologic condition associated with G-protein receptor kinase activity where the G-protein receptor kinase activity would otherwise cause desensitization of a receptor controlling said disease or condition, said method comprising the step of administering NO donor that donates nitric oxide or a related redox species and provides bioactivity that is identified with nitric oxide to inhibit the G-protein receptor kinase activity, thereby sensitizing or preventing desensitization of said receptor.

The term "disease or condition associated with G-protein receptor kinase activity" is used herein to mean a disease or condition resulting from under-stimulation of a GPCR or related insufficient activation of a GPCR.

G-protein receptor kinase activity is described in Pierce, et al, cited above.

The term "controlling said disease or condition" is used herein to mean influence the biochemical or clinical correlate of the disease or condition.

The term "desensitization of a receptor" is used herein to mean decreased activity or decreased level of expression or decreased responsiveness.

The term "to inhibit the G-protein receptor kinase activity" is used herein to mean to decrease its activity.

BRIEF DESCRIPTION OF THE DRAWINGS

FIG. 1 is a graph of heart weight divided by body weight versus control or agent introduced and shows results of Background Example 2.

FIG. 2 is a graph of airway resistance versus allergen challenge at recited concentrations and shows results of Background Example 3.

FIG. 3 is a graph showing effect of GSNO on GRK phosphorylation of a synthetic peptide and shows results of Background Example 4.

DETAILED DESCRIPTION

We turn now to the method of the invention herein which is directed to a method for treating a patient with a disease or pathologic condition associated with G-protein receptor kinase activity where the G-protein receptor kinase activity would otherwise cause desensitization of a receptor controlling said disease or condition, said method comprising the step of administering NO donor that donates nitric oxide or a related redox species and provide bioactivity that is identified with nitric oxide, to inhibit G-protein receptor kinase activity thereby sensitizing or preventing desensitization of said receptor.

The receptors controlling the diseases or conditions are thiol-containing receptors and can be, for example, β-adrenergic receptors, α-adrenergic receptors, $\mu$-opioid receptors and prostaglandin receptors.

Diseases or conditions where a receptor controlling the disease or condition is a β-adrenergic receptor include, for example, right or left heart failure, a patient on a left ventricular heart assist device awaiting heart transplant and a patient who has had heart surgery and otherwise cannot be disconnected from a heart pump without loss of heart function or a patient undergoing surgery who is at risk for a cardiac event. Excluded from invention herein are treatment of pulmonary hypertension and treatment of systemic hypertension which are covered in the parent application hereto.

Diseases or conditions where a receptor controlling the disease or condition is an α-adrenergic receptor include benign prostatic hypertrophy and urinary incontinence.

Patients with diseases or conditions where a receptor controlling the disease or condition is the $\mu$-opioid receptor include patients being treated with an opiate because of pain or a patient addicted to an opiate. Patients being treated with opiates include patients with severe pain because of surgery, cancer or accidental injury. Opiates include, for example, morphine, oxycodone, codeine and meperidine.

Diseases or conditions wherein a receptor controlling the disease or condition is the prostaglandin receptor include inflammatory conditions including rheumatoid arthritis. Cystic fibrosis is included in the case when the NO donor is one capable of acutely lowering FEV1 by more than 12% and the NO donor is administered in a therapeutically effective amount which is insufficient to acutely lower FEV1 by more than 12% (i.e., use of a dose which does not cause bronchodilation); treatment of a patient with cystic fibrosis with nitrolylating agent without regard to limiting dosage, is taught in WO 02/32418.

As indicated above the agents administered herein to inhibit GRK actively are NO donors. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso and N-nitroso compounds and nitro derivatives thereof and metal NO complexes, but not excluding other NO bioactivity generating compounds, useful herein are described in "Methods in Nitric Oxide Research," edited by Feelisch, M., and Stamler, J. S., John Wiley & Sons, New York, 1996, pages 71–115 which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds including S-nitrosothiols useful herein include, for example, S-nitrosoglutathione (GSNO), S-nitroso-N-acetylpenicillamine, S-nitroso-cysteine and ethyl ester thereof, S-nitroso cysteinyl glycine, S-nitrosogamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, nitroglycerin, SIN1 which is molsidomine, furoxamines, N-hydroxy (N-nitrosamine) and perfluorocarbons that have been saturated with NO or a hydrophobic NO donor. A preferred NO donor for use herein is GSNO. When GSNO is administered in the treatment of a disease or pathologic condition where the receptor controlling said disease or condition is a β-adrenergic receptor, the GSNO functions to sensitize or prevent desensitization of the receptor as well as to increase heart pumping action as well as to provide the effect of an α-adrenergic agonist of maintaining or increasing blood pressure and also to activate ryanodine receptor so it releases calcium resulting in improved contractility.

The amount of NO donor administered is an amount which causes the receptor to control the disease or pathologic condition controlled by it and sensitizes or prevents desensitization of said receptor. An amount that sensitizes or prevents desensitization of a receptor can be determined by pharmacological or clinical response or by receptor binding studies. The dosage of NO donor administered in the case of a patient with heart failure, or who is connected to a left ventricular heart assist device awaiting heart transplant or who has had heart surgery and otherwise cannot be disconnected from a heart pump without loss of heart function, is a dosage that increases heart pumping function and in the case of GSNO is a dosage which also stimulates growth of heart muscle. The dosage of NO donor for an operative procedure is one which protects from a coronary event. The dosage of NO donor for a patient being treated with or who is addicted to an opiate is a dosage which stabilizes or reduces the dosage of opiate to obtain a particular level of effect. The dosage of NO donor for an inflammatory condition is an inflammation ameliorating effect, e.g., to ameliorate bronchoconstriction and hypoxia and prevent the long term deterioration of lung function, dyspnea, cough, chronic airway infection, bronchiectasis, atelectasis and pneumonothorax in patients with cystic fibrosis and in the case of rhematoid arthritis to reduce joint inflammation and tenderness and synovial thickening and joint stiffness.

In general, administering an effective amount of NO donor involves administration to achieve an amount of NO donor in the blood of 100 picomolar to 100 micromolar depending on the agent administered and the disease or condition treated.

Preferably the NO donor is administered in a therapeutically effective amount which is insufficient to lower mean arterial blood pressure or pulmonary artery pressure by more than 10%.

When GSNO is the treating agent, it is preferably administered at a dosage ranging from 0.01 nmol/kg/min to 1000 nmol/kg/min, very preferably from 0.1 to 10 nmol/kg/min. For diseases or conditions where a receptor controlling the disease or condition is a β-adrenergic receptor, the GSNO or NO donor is preferably administered in amount which both increases the pumping action of the heart and causes growth of heart muscle and very preferably in conjunction with a β-adrenergic receptor agonist, e.g., isoproterenol, dobutamine or dopamine. The β-adrenergic receptor agonist is preferably administered in an amount which increases pumping action of the heart. For isoproterenol, this dosage ranges from 0.5 to 50 μg/min.

Administration of the NO donor treating agents have benefit in the case of patient with chronic heart failure regardless of whether β-adrenergic agonist has or is being administered. It is known that in chronic heart failure, catecholamines are highly elevated and thus the receptor may be down regulated and/or the system desensitized, and that β-adrenergic agonists and other inotropic agents can kill patients, if used chronically because of further down regulation and desensitization. Thus NO donor functioning as a GRK inhibitor, used without β-adrenergic agonist administration, provides a unique therapeutic benefit. Moreover, as indicated above, NO donor treating agent has a benefit in the case of patients with chronic heart failure, when administered conjointly with β-adrenergic agonist.

The invention is supported by the following background examples and illustrated by the following working examples:

BACKGROUND EXAMPLE 1

Mice were treated with 10 ng/kg/day of GSNO or PBS infused continuously for 1 week through an azlet miniosmotic pump placed subcutaneously. Another set of mice was treated for 7 days with isoproterenol (30 mg/kg/day), and the fourth and final group received for 7 days, isoproterenol (30 mg/kg/day) plus GSNO (10 ng/kg/day). The mice were sacrificed and heart tissue was removed. Saturation binding with radiolabeled $I^{125}$-cyanopindolol was carried out in purified cardiac membrane according to the procedure of Iaccarino et al, Circulation 98, 17A3–17A9 (1998). For mice not treated with GSNO or isoproterenol, the amount of β-adrenergic receptor was determined to be 40–50 fmol per mg protein. For mice not treated with GSNO but treated with isoproterenol (30 mg/kg/day), the amount of β-adrenergic receptor was determined to be 20 fmol per milligram protein, demonstrating receptor down-regulation. For mice treated with GSNO but not isoproterenol, the amount of β-adrenergic receptor was determined to be 40 fmol per mg/protein or the same as for normal mice (no GSNO or isoproterenol). For mice treated with GSNO and isoproterenol (30 mg/kg/day), the amount of β-adrenergic receptor was determined to be 90 fmol per mg protein. The experiment shows that GSNO prevents desensitization and down-regulation of β-adrenergic receptors caused by isoproterenol and stimulates expression of the β-adrenergic receptors.

BACKGROUND EXAMPLE 2

Mice were treated with 10/ng/kg/day of GSNO, or with PBS (control) or with isoproterenol (at a dosage of 30 mg/kg/day) or with 10 mg/kg/day of GSNO plus 30 mg/kg/day isoproterenol, infused continuously for 1 week. The animals were sacrificed and the hearts were weighed and a ratio of heart weight to body weight was determined for each case. The results are set forth in FIG. 1 where hw:bw, i.e., the legend on the vertical axis, is the ratio of heart weight to total body weight and "ISO" means isoproterenol. As shown in FIG. 1, GSNO treatment increases the size of the heart muscle consistent with preventing desensitization of the β-adrenergic receptor. Treatment with isoproterenol also increased the size of the heart muscle. The combination of isoproterenol plus GSNO has even more effect in increasing size of heart muscle. The increase in size of heart (hypertrophy) is an advantage especially in the case of a patient on a left ventricular heart assist device awaiting heart transplant and in the case of a patient who has had heart surgery and cannot be disconnected from a heart pump without loss of heart function. The asterisks in FIG. 1 mean p>0.05 compared to control.

BACKGROUND EXAMPLE 3

Figure 2:
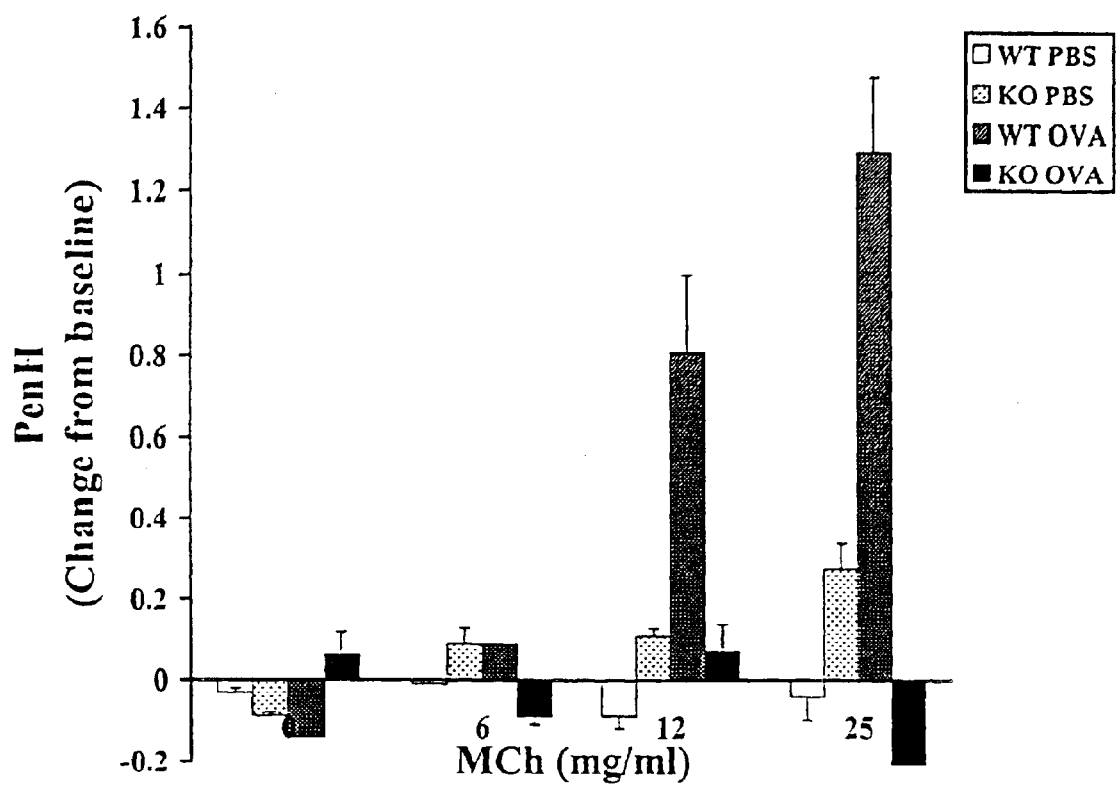

Mice having normal GSNO reductase (wild type or WT) and GSNO reductase knockout mice (KO), that is with GSNO reductase knocked out thereby having increased level of GSNO, were tested for responsiveness to airway provocation. The mice were challenged with phosphate buffered saline (PBS) or ovalbumin (OVA) according to the procedure of described in Drazen, J., et al, Annual Rev. Physiology 61, 593–625 (1999). Mice were sensitized to ovalbumin (OVA) by intraperitoneal injection 2 weeks prior to airway challenge. Baseline airway resistance measurements (PenH) were performed on mice after methacholine challenge (MCh) followed by airway challenge 24 hours later with aerosolized PBS or OVA. The mice challenged with aerosolized saline (PBS) served as the control group. The results are shown in FIG. 2 where PenH is airway resistance and MCh is methacholine challenge. As shown in FIG. 2, the wild type mice showed a significant increase in airway resistance after OVA challenge at methacholine concentrations of 12 and 25 mg/ml whereas the KO mice had no change. The results suggest that GSNO administration will cause hyporesponsiveness to allergen challenge further suggesting that the GSNO causes sensitizing or prevents desensitization of the appropriate GPCRs, e.g., prostaglandin receptors.

BACKGROUND EXAMPLE 4

Figure 3:
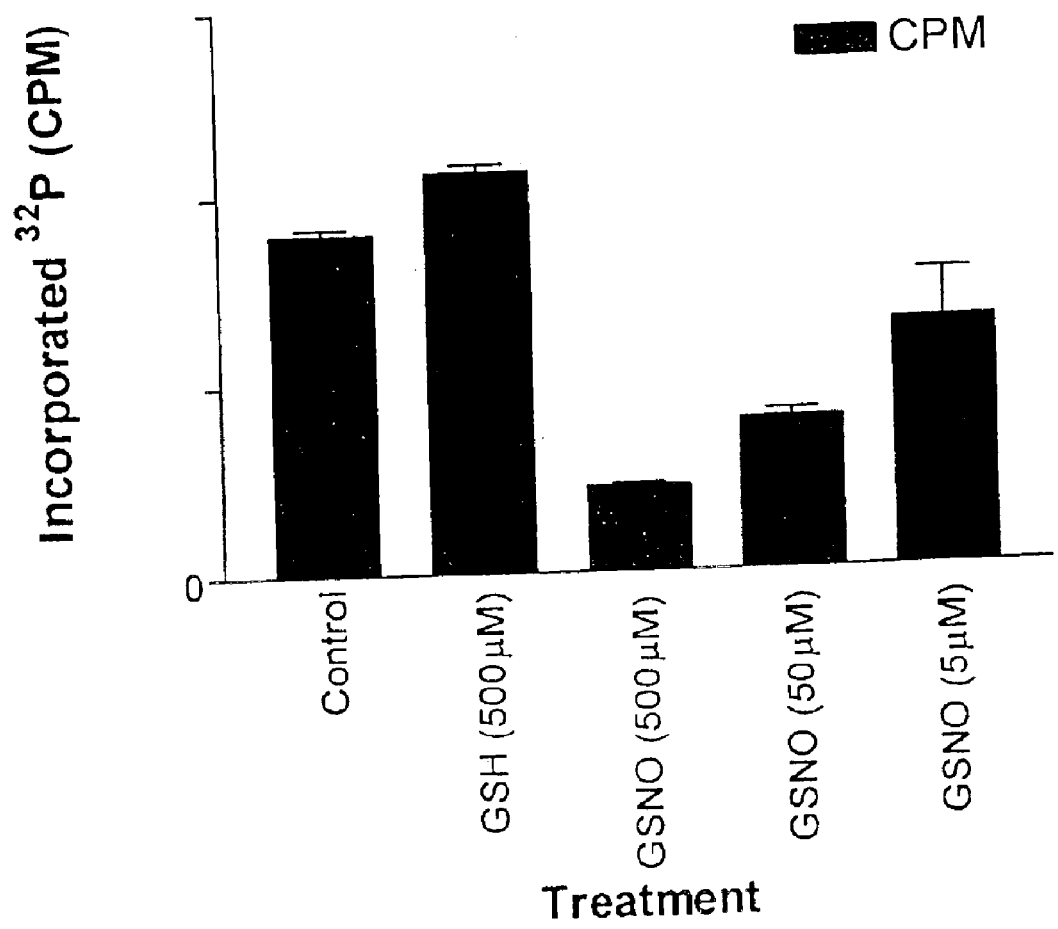

An isolated system was provided consisting of medium, GRK, standard synthetic peptide substrate and radiolabeled $^{32}$P-adenosine triphosphate, i.e., $^{32}$P-ATP, as a source of phosphate. Runs were carried out on the system without additives, and with 500 µM glutathione (GSH) present and with GSNO (500 µM) present or with GSNO (50 µM) present or with GSNO (5 µm) present. The amount of bound $^{32}$P was measured in counts per minute (CPM). The results are shown in FIG. 3 where there is shown a concentration dependent reduction in incorporation of $^{32}$P when GSNO is present. The results suggest that GSNO inhibits GRK to inhibit phosphorylation of substrate (incorporated $^{32}$P). The same result of GRK inhibition and interference with substrate phosphorylation was found when S-nitroso-cysteine (L-SNC) was substituted for GSNO.

EXAMPLE I

A 65-year old with class 4 congestive heart failure enters the hospital with shortness of breath and bradyacardia. He is given 10 µg per minute of intravenous isoproterenol with resolution of symptoms. The patient is subsequently switched to IV dobutamine at 10 µg per kg per minute titrated to cardiac output. Over the following three days the drug is increased to 30 µg per kg per minute to maintain cardiac output. The patient is then begun on IV GSNO at 2 nmol per kg per minute and cardiac output improved over the following 24 hours. The dose of dobutamine is subsequently decreased gradually and then stopped. The patient undergoes bypass surgery and does well even though he has been viewed as at high risk.

EXAMPLE II

A 49-year old white male awaiting cardiac transplantation is placed a left ventricular assist device, but continues to suffer from severe shortness of breath. He is begun on IV GSNO 4 nmol per kg per minute with decrease in shortness of breath and an increase in cardiac output.

EXAMPLE III

A 68-year old white female with an ejection fraction of 17% undergoes coronary artery bypass grafting. The surgeons are unable to remove the patient from bypass. Intravenous GSNO is begun at 2 nmol per kg per minute and after two hours the patient is successfully removed from bypass.

EXAMPLE IV

A 75-year-old white male with metastatic prostate cancer is suffering from severe bone pain unresponsive to opiates. He is begun on intravenous GSNO at 10 nmol per kg per minute in conjunction with morphine which now relieves his pain.

EXAMPLE V

A 29-year-old heroine addict enters a clinic where his dose is tapered gradually. In order to avoid symptoms of withdrawal, ethyl nitrite is started intravenously at 2 nmol per kg per minute and symptoms of withdrawal, including sweats and shaking, are ameliorated.

EXAMPLE VI

A 17-year-old white female with cystic fibrosis enters the hospital complaining of shortness of breath. She is begun on inhaled beta agonists, but shows little improvement over the following six days. She is started on inhaled GSNO (3 cc of a 10 mM solution, pH 7, 4x/day). Although her FEV1 does not change acutely and her blood pressure remains stable, symptoms of shortness of breath resolve over the following 48 hours (with corresponding improvement in FEV1).

EXAMPLE VII

A 66-year-old white female with rheumatoid arthritis and pulmonary infiltrates complains of shortness of breath and knee pain. She is begun on intravenous ethyl nitrite at 2 nmol per kg per minute with improvement in respiratory status and a decrease in knee pain.

Variations

Variations on the above will be obvious to those skilled in the art. Therefore the scope of the invention is to be determined by the claims.

What is claimed is:

1. A method of treating a disease or pathologic condition associated with G-protein receptor kinase activity in a patient where the disease or pathologic condition is addiction to an opiate and the G-protein receptor kinase activity would otherwise cause desensitization of a $\mu$-opioid receptor controlling said addiction, said method comprising the step of administering ethyl nitrite to said patient.

2. A method of treating a disease or pathologic condition associated with G-protein receptor kinase activity in a patient where the disease or pathologic condition is rheumatoid arthritis and where the G-protein receptor kinase activity would otherwise cause desensitization of a receptor controlling said rheumatoid arthritis, said method comprising the step administering ethyl nitrite to said patient.

* * * * *